(12) United States Patent
Anderson

(10) Patent No.: US 8,807,133 B2
(45) Date of Patent: Aug. 19, 2014

(54) RESUSCITATOR AND ASPIRATOR TECHNOLOGY

(76) Inventor: Mark Anderson, Spring Valley, WI (US)

(*) Notice: Subject to any disclaimer, the term of this patent is extended or adjusted under 35 U.S.C. 154(b) by 140 days.

(21) Appl. No.: 13/009,722

(22) Filed: Jan. 19, 2011

(65) Prior Publication Data

US 2011/0174309 A1    Jul. 21, 2011

Related U.S. Application Data

(60) Provisional application No. 61/336,228, filed on Jan. 19, 2010.

(51) Int. Cl.
| A61D 7/04 | (2006.01) |
| A61D 1/08 | (2006.01) |
| A61M 16/06 | (2006.01) |
| A61M 16/00 | (2006.01) |

(52) U.S. Cl.
CPC ... *A61D 7/04* (2013.01); *A61D 1/08* (2013.01); *A61M 16/06* (2013.01); *A61M 16/0057* (2013.01); *A61M 16/0084* (2013.01)
USPC ............ 128/205.18; 128/205.17; 128/205.13; 128/204.18; 128/200.24

(58) Field of Classification Search
CPC ..... A61M 16/00; A61M 16/04; A61M 16/06; A61M 16/0463; A61M 16/0057; A61M 16/0084; A61M 16/0078; A61M 16/08; A61M 16/0404; A61M 5/14236; A61M 1/0066; A61M 1/0058

USPC .......................... 128/200.24, 202.28–203.11, 128/205.13–205.17

See application file for complete search history.

(56) References Cited

U.S. PATENT DOCUMENTS

| 3,730,179 | A | * | 5/1973 | Williams | 128/204.18 |
| 3,794,026 | A | * | 2/1974 | Jacobs | 128/200.13 |
| 4,141,355 | A | * | 2/1979 | Apple | 128/205.18 |
| 4,539,985 | A | * | 9/1985 | Magrath | 128/205.13 |
| 4,655,213 | A | * | 4/1987 | Rapoport et al. | 128/205.25 |
| 4,898,167 | A | * | 2/1990 | Pierce et al. | 128/205.16 |
| 5,676,133 | A | | 10/1997 | Hickle et al. | |
| 5,934,510 | A | | 8/1999 | Anderson | |
| 5,975,081 | A | * | 11/1999 | Hood et al. | 128/845 |
| 6,253,961 | B1 | | 7/2001 | Anderson | |
| 6,364,170 | B1 | | 4/2002 | Anderson | |
| 6,488,029 | B1 | * | 12/2002 | Hood et al. | 128/845 |
| 6,494,209 | B2 | * | 12/2002 | Kulick | 128/848 |
| 6,840,923 | B1 | * | 1/2005 | Lapcevic | 604/319 |
| 6,899,103 | B1 | * | 5/2005 | Hood et al. | 128/845 |
| 2008/0257351 | A1 | * | 10/2008 | Gitschlag | 128/205.13 |
| 2010/0122699 | A1 | * | 5/2010 | Birnkrant | 128/204.21 |

* cited by examiner

*Primary Examiner* — Annette Dixon
(74) *Attorney, Agent, or Firm* — Skinner and Associates; Joel Skinner

(57) ABSTRACT

An aspiration and resuscitation system which is useable to perform aspiration and/or resuscitation procedures on living beings, particularly small animals, and most particularly newborn small animals such as puppies and kittens. The system includes an aspirator and a resuscitator. Each includes a separable pump and animal interface mask. Further disclosed are aspiration and resuscitation methods using the disclosed apparatus.

13 Claims, 3 Drawing Sheets

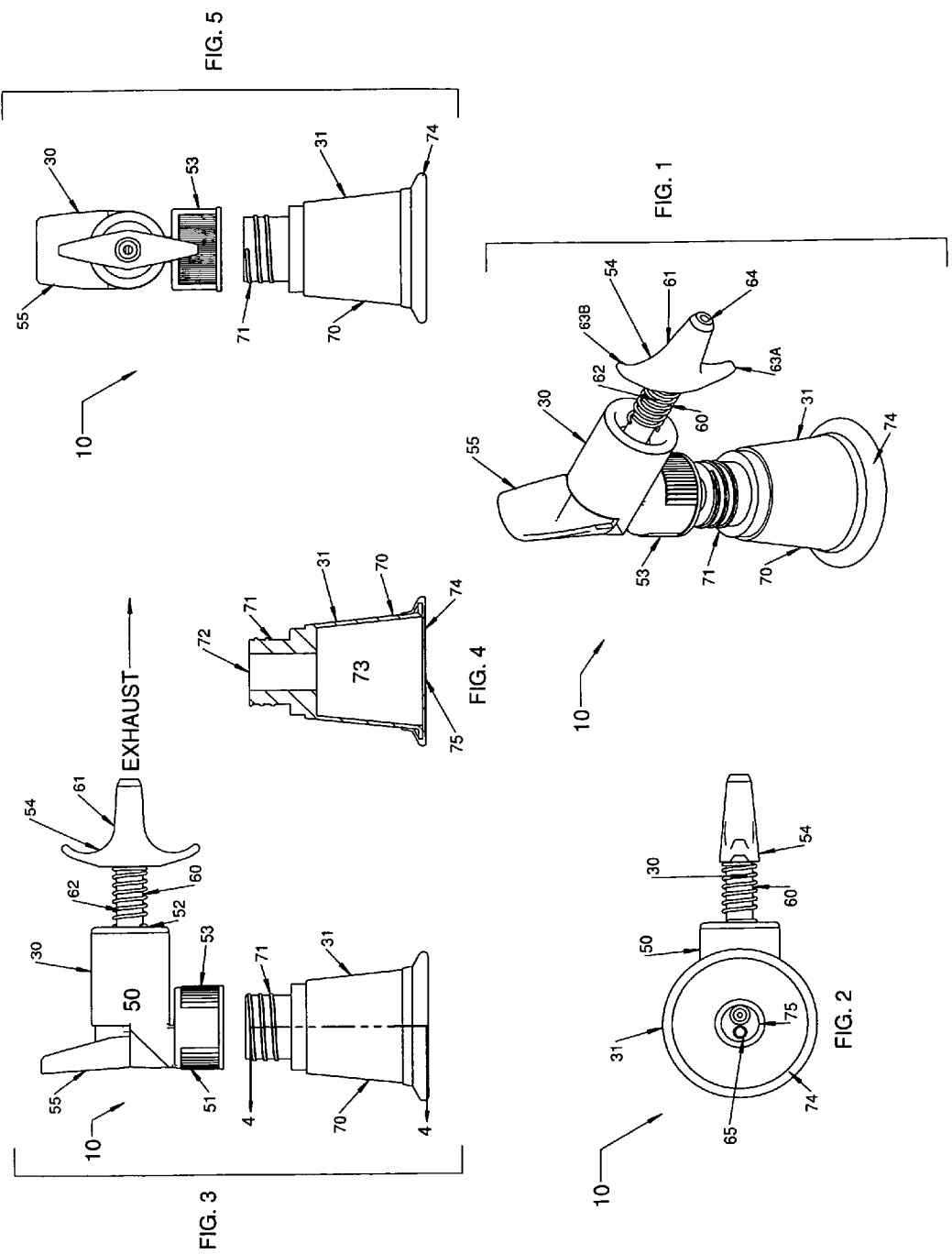

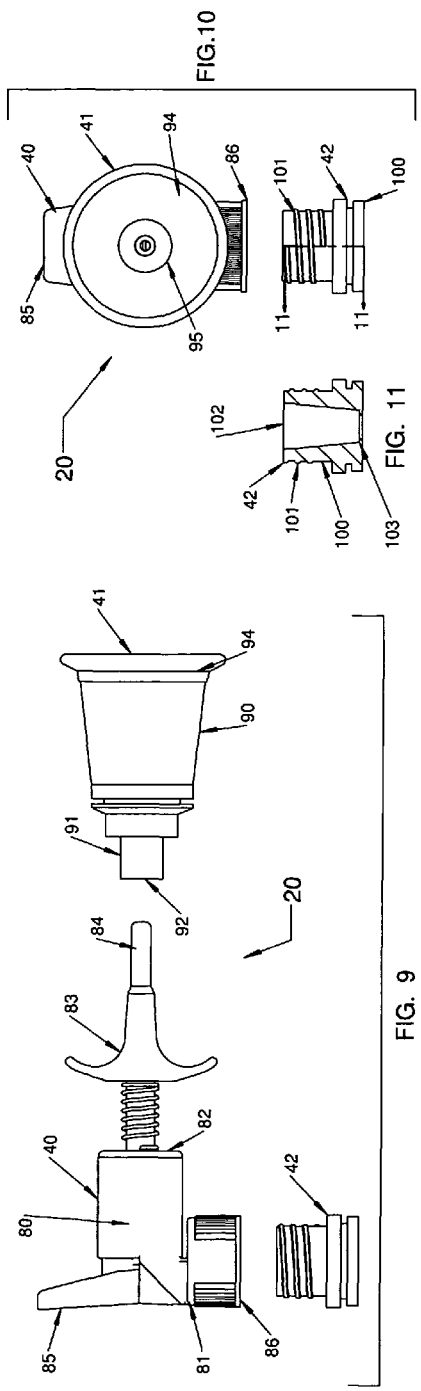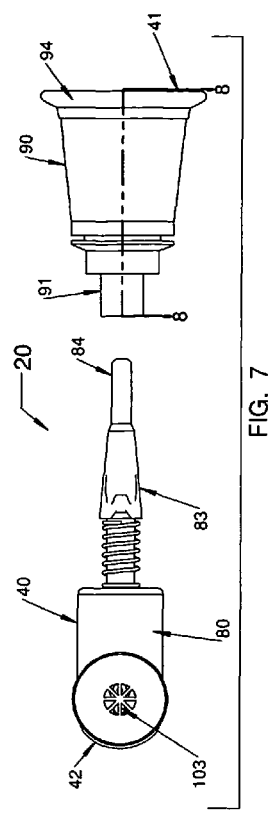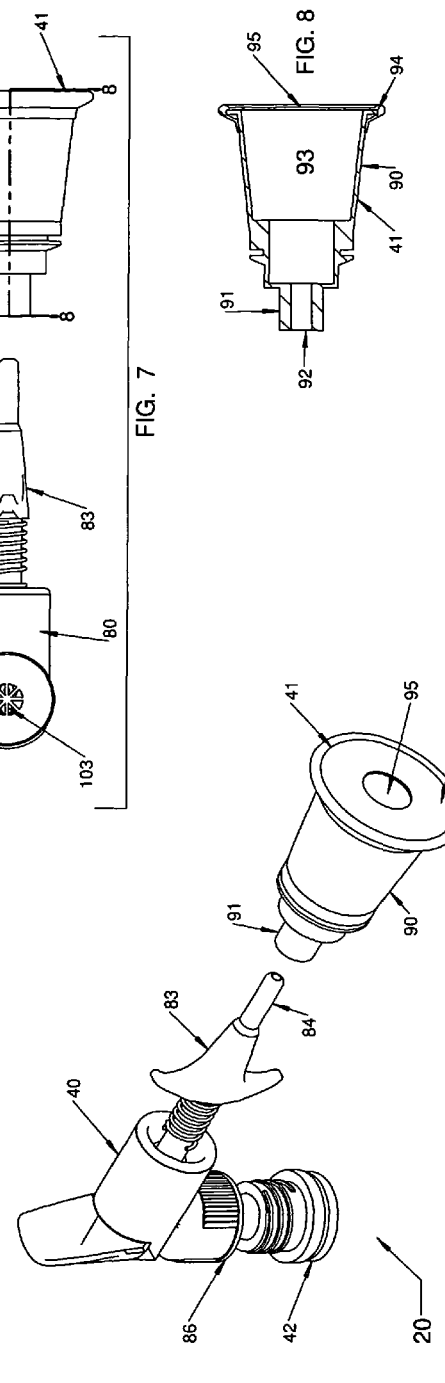

RESUSCITATOR AND ASPIRATOR TECHNOLOGY

CROSS-REFERENCE TO RELATED APPLICATIONS, IF ANY

This application claims the benefit under 35 U.S.C. §119(e) of co-pending U.S. Provisional Patent Application Ser. No. 61/336,228, filed Jan. 19, 2010, which is hereby incorporated by reference.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to medical systems, apparatus and methods. Particularly, the invention relates to veterinary medical systems, apparatus and methods. Most particularly, the invention relates to an aspirator and resuscitator system, apparatus and method useable for small animals such as dogs, cat and the like, particularly for newborn small animals such as puppies and kittens.

2. Background Information

Existing technology in this field is believed to have significant limitations and shortcomings. For this and other reasons, a need exists for the present invention.

All U.S. patents and patent applications, and all other published documents mentioned anywhere in this application are incorporated by reference in their entirety.

BRIEF SUMMARY OF THE INVENTION

The invention provides an aspiration and resuscitation system, apparatus and method which are practical, reliable, safe and efficient, and which are believed to fulfill the need and to constitute an improvement over the background technology.

It is not uncommon for puppies and kittens to be born with clogged breathing passages, especially after C-section births, and which can be life threatening if not treated immediately. The invention provides a system to clear breathing pathways and to stimulate the first breaths of newborn animals such as puppies, kittens and other small companion animals. The system provides a non-invasive apparatus that can be used safely and effectively by veterinary professionals and pet owners with reduced risk of causing harm to the newborn. The system provides controlled, safe vacuum suction and air supply for respiratory stimulation response for the respective specific aspiration and resuscitation procedures. The system enables the user to stimulate the proprioceptive receptors of the patient to engage involuntary respirative efforts. By providing these fundamentals at a time of potential stress, the system enables the specific weakened newborn patient to have an optimum opportunity in sequencing its own internal cognitive physiological response this inhaling and exhaling on its own.

One aspect of the invention provides complementary aspirator and resuscitator which are useable to perform aspiration and resuscitation procedures on living beings, particularly small animals and most particularly newborn small animals such as puppies, kittens and the like. The aspirator and resuscitator each includes a pump and animal interface masks.

In another aspect, the invention provides a system for aspirating and resuscitating a patient comprising an aspirator including a suction pump connected to a patient aspiration mask, and a resuscitator including an air supply pump connected to a patient resuscitation mask.

In a further aspect, the invention provides a system for aspirating and resuscitating a newborn small animal patient such as a puppy, kitten or small companion animal, including:
 a. an aspirator including a suction pump selectively connectible and disconnectible to a patient aspiration mask, the aspirator suction pump having a piston pump body with a suction port for connection to the patient aspiration mask and a pump actuator including an exhaust port, and the patient aspiration mask having a mask body with a pump connection end for mating with the aspirator suction pump and a flexible diaphragm disposed at an opposite end with an diaphragm aperture for placement on the nose or mouth of a patient, and
 b. a resuscitator including an air supply pump selectively connectible and disconnectible to a patient resuscitation mask, the resuscitator air supply pump having a piston pump body with an air ingress port and a pump actuator including an air egress port for connection to the patient resuscitation mask, the patient resuscitation mask having a mask body with a friction fit pump connection end for mating with the resuscitator air supply pump and a flexible diaphragm disposed at an opposite end with an diaphragm aperture for placement on the nose or mouth of a patient.

In yet another aspect, the invention provides a method of aspirating and resuscitating a patient including the steps of:
 a. aspirating the patient by
  i. providing an aspirator including a suction pump connected to a patient aspiration mask,
  ii. placing the patient aspiration mask on the patient and
  iii. actuating the suction pump; and
 b. resuscitating the patient by
  i. providing a resuscitator including an air supply pump connected to a patient resuscitation mask,
  ii. placing the patient resuscitation mask on the patient; and
  iii. actuating the air supply pump.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 1 is a perspective view of an embodiment of an aspiration device of an embodiment of the aspiration and resuscitation system of the present invention.

FIG. 2 is a bottom view of the aspirator.

FIG. 3 is a side view, with components exploded, of the aspirator.

FIG. 4 is a crossectional view of an embodiment of the aspirator mask component of the aspirator, taken along line 4-4 of FIG. 3.

FIG. 5 is an end view of the aspirator with components separated.

FIG. 6 is a perspective view of an embodiment of a resuscitation device of the aspiration/resuscitation system of the present invention.

FIG. 7 is a top view, with components exploded, of the resuscitator.

FIG. 8 is a crossectional view of an embodiment of the resuscitator mask component of the resuscitator, taken along line 8-8 of FIG. 7.

FIG. 9 is a side view, exploded, of the resuscitator.

FIG. 10 is an end view of the resuscitator.

FIG. 11 is a crossectional view of an embodiment of the intake component of the resuscitator, taken along line 11-11 of FIG. 10.

DETAILED DESCRIPTION

Figures 12A, 12B:
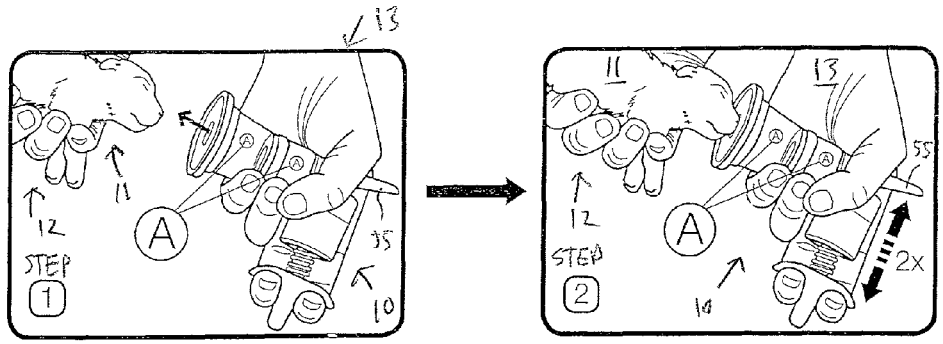
FIGS. 12 A-H illustrate an embodiment of the method of using the aspirator and resuscitator components of the aspiration/resuscitation system of the invention to aspirate, resuscitate, or aspirate and resuscitate a small animal such as a puppy.
Figures 12C, 12D:
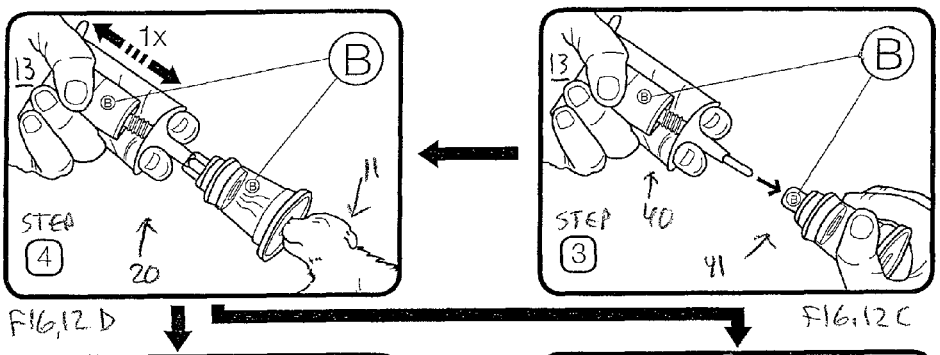
Figure 12E:
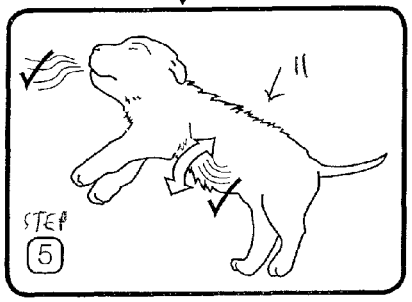
Figure 12F:
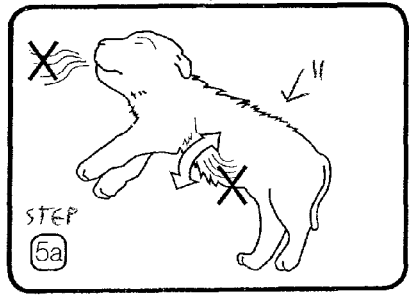
Figure 12H:
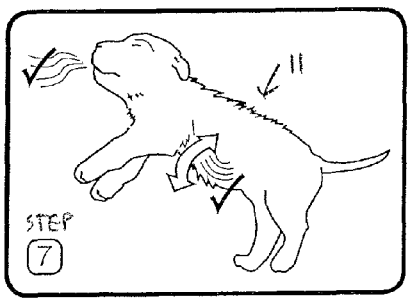
Figure 12G:
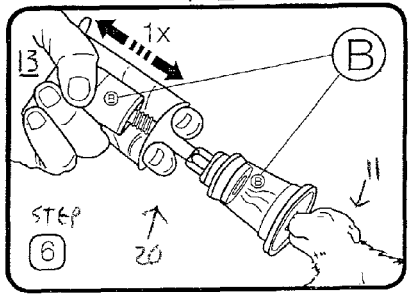

The invention provides a system for aspirating, resuscitating, or aspirating and resuscitating living beings. The unit 10 is especially useful for aspirating and resuscitating small animals, particularly newborn small animals such as puppies, kittens and the like. The primary system aspirator 10 and resuscitator 20 components shown in use to aspirate and then resuscitate a puppy 11 in FIG. 12 where the user is holding the patient puppy 11 one hand 12 and the apparatus 10/20 in the other hand 13.

Referring to FIG. 1, a preferred embodiment of the aspirator 10 of the present invention includes a pump 30 and a mask 31. The pump 30 and mask 31 are preferably separate components which are connectible and disconnectible to facilitate storage, transportation, cleaning, adjustment and replacement. It is however within the purview of the invention that the pump and mask 30 and 31 may be constructed as a single, integral unit. As is best shown in FIGS. 12 A and B, the aspirator 10 is of a size that it can be easily, accurately and effectively be held in one hand of a user, for example a veterinarian or veterinary technician.

Referring also to FIGS. 2-5, the aspirator pump 30 has a main body portion 50 with a suction end 51 and an exhaust end 52. The body 50 has a cylindrical configuration with a mask connector 53 (also cylindrically shaped) disposed at the suction end 51. The hollow interior of the body 50 serves as a cylinder of a predetermined volume. A piston is disposed in the body towards the exhaust end 52. The suction end of the cylinder is communicatively connected to the exterior via a suction aperture 65 (best shown in FIG. 2) The mask connector 53 has a knurled exterior and a threaded (for connection) interior. Preferably, the mask connector 53 is disposed at a right angle with respect to the central axis of the pump body 50. A plunger assembly 54 is disposed at the exhaust end 52 of the body 50. The plunger assembly 54 preferably has a hollow shaft 60 which is connected to the piston and surrounded by a spring 62, and an actuator end piece 61. The end piece 61 has a pair of triggers 63 A and B extending laterally outwardly for engagement by the user's fingers. The end piece 61 has a distal exhaust aperture 64 that is communicatively connected to a central axial exhaust port which extends through the end piece 61 and shaft 60 to the pump body 50 cylinder, through the piston. The spring 62 holds the end piece 61 in a normally extended position away from the body 50. This also holds the piston towards the exhaust end 52 of the body 50. Actuation by the user by pulling the end piece 61 towards the body 50 (against the bias of the spring 62) extends the piston into the cylinder. Air is expelled through the exhaust aperture 64. When the end piece 61 is released by the user, the spring 61 pushes it outwardly, pulling the shaft 20 and piston along with it. The resultant expansion of the cylinder sucks air at the suction aperture 65. The pump 30 components, with the exception of the spring 62, are preferably constructed of polymeric materials.

In cooperation with the size of the pump 30, its right angle construction with respect to the mask connector 53 and end piece 63, and the triggers 63, a palm brace 55 extends from the body 50 to further facilitate holding and actuation of the aspirator 10 in one hand 13 of the user so that the other hand 12 may hold the patient 11 or perform other tasks, for example as shown in FIGS. 12 A and B.

With particular attention to FIG. 4, a preferred embodiment the aspiration mask 31 includes a frusto-conical body 70 having a connection end 71 with external threads for mating with the mask connector 53. The body 70 has a hollow interior 73 of a predetermined volume. The connection end has a proximal aperture 72 for communicative connection with the fluid flow portions of the pump 30. The distal end of the body 70 has a flexible diaphragm 74 with a central aperture 75. In use, the aperture 75 is placed over the nose or nose and mouth of the patient. The diaphragm 74 is thin and soft and cushions the interface with the patient. The flexible nature of the diaphragm 74 also dampens and moderates the suction power of the aspirator 10. The mask 31 components are also preferably constructed of polymeric materials. The body 70 is preferably constructed of clear, transparent material so that any material such as fluid, mucus and the like aspirated from the patient during actuation described above, is visible to the user.

Suitable embodiments of the pump 20 are described in U.S. Pat. Nos. 5,934,510, 6,253,961 and 6,364,170, which are owned by applicants assignee, and which are all incorporated by reference in their entirety. Pumps of this type are manufactured and or sold buy applicant's assignee, MAI/Genesis of Spring Valley, Wis., USA.

Referring to FIG. 6, a preferred embodiment of the resuscitator 20 of the present invention includes a pump 40, a mask 41 and an air intake member 42. The pump 40, mask 41 and air intake member 42 are preferably separate components which are connectible and disconnectible, but again they may be constructed as a single, integral unit. As is best shown in FIG. 12 C-F, the resuscitator 20 is also of a size such that it can be held in one hand of a user.

Referring also to FIGS. 7-11, the resuscitator pump 40 has a main body portion 80 with an air ingress end 81 and an air egress or exhaust end 82. The resuscitator pump 40 has a structure and function which are substantially similar to the structure and function of the aspirator pump 30 described above. One difference is that the resuscitator pump 40 air supply cylinder volume is larger (approximately twice the size) than that of the aspirator pump 30 to provide more exhaust air to the patient. The preferred volume of air delivery to stimulate respiratory response is approximately 10 ml. The pump 40 has an actuation plunger assembly 83 with a distal mask connection end 84. The outside diameter of the end 84 has a dimension which is substantially equivalent to the inside diameter of a complementary connection element 91 of the mask 41 whereby they may be connected and disconnected via a friction fit. A palm support 85 is disposed on the outside of the pump 40. And, a threaded intake connector 86 is disposed at the air intake end 81 of the pump 41.

A preferred embodiment the resuscitator mask 41 also includes a frusto-conical body 90 having a connection end 91 with a predetermined friction fit configuration for mating with the resuscitator connection end 84 and with a standard medical oxygen supply fitting. The body 90 has a hollow interior 93 of a predetermined volume. The connection end has a proximal aperture 92 for communicative connection with the fluid flow portions of the pump 40. The distal end of the body 90 has a flexible diaphragm 94 with a central aperture 95. In use, the aperture 95 is placed over the nose or nose and mouth of the patient 11. The diaphragm 94 is thin and soft and cushions the interface with the patient. The flexible nature of the diaphragm 94 also dampens and moderates the air supply power of the resuscitator. The mask 41 components are also preferably constructed of polymeric materials. The body 90 is preferably constructed of clear, transparent material so that the patient's mouth and nose can be visually monitored during resuscitation actuation.

The air intake member 42 is connected to the connector 86 of the pump 40 preferably via screw threads. As is best shown in FIGS. 10 and 11, the air intake member 42 has a cylindrical configuration with a polymeric body 100. external screw threads, 101, a proximal aperture 102 and a distal air intake aperture 103.

Although the aspirator 10 and resuscitator 20 of the system have been shown and described as separate devices or apparatus, it is within the purview of the invention that the system could be constructed using a single pump and modifying the connection ends to attach aspiration and resuscitation masks and intakes.

Referring to FIGS. 12A and 12B, in use, during an aspiration procedure, an aspirator 10 (pump and mask elements "A") is grasped by the user and the aspiration mask 31 is placed on the mouth of the animal 11, for example the muzzle of a puppy 11. Preferably, the animal should be placed or held head facing downward at an angle of between 45 and 90 degrees from the horizon. The pump 30 is actuated by hand 13. Utilizing the aspirator 10 shown and described above, two (2) complete actuation cycles or pumps are made. Each cycle or pump involves a depression and a corresponding release. The pump 30 draws air away from the mask 31. A predetermined mild vacuum is created which causes mucus or fluids that may be blocking the airway of the patient 11 to be drawn out of the patient 11 and into the mask 31. The thoracic area behind the front legs and in front of the stomach of the puppy or kitten should be gently massaged. After aspiration, the mask 31 is removed from the patient 11 and the patient should be checked for breathing reflex. A resuscitation procedure may then be performed if the patient is not breathing.

Referring to FIGS. 12 C-E, in use during a resuscitation procedure, a resuscitator 20 (pump and mask elements "B") is obtained by the user and the resuscitation mask 41 is placed on the mouth of the animal 11, for example the muzzle of a puppy and the pump 40 is actuated by hand 13. Utilizing the resuscitator 20 shown and described above, one (1) actuation cycle or pump is made. The pump 40 pumps air into the mask 41 and into the lungs of the patient 11. Breathing should be stimulated thereafter. After resuscitation, the mask 41 is removed from the patient 11. Referring also to FIGS. 12 F-H, further resuscitation or aspiration procedures may be repeated as deemed medically necessary by the user.

During both aspiration and resuscitation, patients must be handled properly with passage ways cleared of potential blockages around the nostrils and mouth areas. Stimulation is important, so massage should be applied to the thorax area. The resuscitator should not be used for continuous pumping because the goal is for the patient's involuntary act of breathing to be initiated through stimulation of the respiratory response.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A portable, veterinary medical system for aspirating and resuscitating a newborn small companion animal, comprising a hand-held, hand powered aspirator adapted to be held and operated by one hand, the aspirator including a piston based suction pump connected to a patient aspiration mask that is adapted to be fit over the muzzle of the newborn small animal patient, the suction pump having an exhaust port for exhausting aspirated material, and a hand-held, hand powered resuscitator adapted to be held and operated by one hand, the resuscitator including a piston based air supply pump connected to a patient resuscitation mask that is adapted to fit over the muzzle of the newborn small animal patient, the air supply pump having an air ingress port for taking air in during resuscitation.

2. The system of claim 1, wherein the aspirator suction pump and the patient aspiration mask are disconnectible and connectible, and the resuscitator air supply pump and patient resuscitation mask are disconnectible and connectible.

3. The system of claim 2, wherein the aspirator suction pump and patient aspiration mask have complementary screw threaded connections, and wherein the resuscitator air supply pump and patient resuscitation mask have complementary friction fit connections.

4. The system of claim 1, wherein the aspirator suction pump has a pump body with a suction port for connection to the patient aspiration mask and a pump actuator including the exhaust port.

5. The system of claim 1, wherein the resuscitator air supply pump has a pump body with the air ingress port and a pump actuator including an air egress port for connection to the patient resuscitation mask.

6. The system of claim 5, further comprising an air intake member connected to the air ingress port.

7. The system of claim 1, wherein the resuscitator air supply pump delivers approximately 10 ml of air per pump actuation.

8. The system of claim 1, wherein the patient aspiration mask has a mask body with a screw threaded pump connection end for mating with the aspirator suction pump and a flexible diaphragm disposed at an opposite end with an diaphragm aperture for placement on the muzzle of a patient.

9. The system of claim 8, wherein the mask body is constructed of a transparent material whereby the user can visualize the patient's nose and mouth during aspiration.

10. The system of claim 1, wherein the patient resuscitation mask has a mask body with a friction fit pump connection end for mating with the resuscitator air supply pump and a flexible diaphragm disposed at an opposite end with an diaphragm aperture for placement on the muzzle of a patient.

11. The system of claim 10, wherein the mask body is constructed of a transparent material whereby the user can visualize the patient's nose and mouth during resuscitation.

12. A portable, veterinary medical system for aspirating and resuscitating a newborn small animal patient, comprising:
   a. hand-held aspirator adapted to be held and operated by one hand, the aspirator including a hand powered suction pump selectively connectible and disconnectible to a patient aspiration mask, the aspirator suction pump having a piston pump body with a suction port for connection to the patient aspiration mask and a finger pump actuator including an exhaust port, and the patient aspiration mask having a mask body with a pump connection end for mating with the aspirator suction pump and a flexible diaphragm disposed at an opposite end with an diaphragm aperture for placement over the newborn small animal patient's muzzle covering the nose and mouth of a patient, wherein the aspirator suction pump and patient aspiration mask have complementary screw threaded connections, and wherein the mask body is constructed of a transparent material whereby the user can visualize the newborn small animal patient's nose and mouth during aspiration, and
   b. a hand-held resuscitator adapted to be held and operated by one hand, the resuscitator including a hand powered air supply pump selectively connectible and disconnectible to a patient resuscitation mask, the resuscitator air supply pump having a piston pump body with an air ingress port and a finger pump actuator including an air egress port for connection to the patient resuscitation mask, wherein the resuscitator air supply pump delivers approximately 10 ml of air per pump actuation, the patient resuscitation mask having a mask body with a friction fit pump connection end for mating with the resuscitator air supply pump and a flexible diaphragm disposed at an opposite end with an diaphragm aperture for placement over the newborn small animal patient's muzzle covering the nose and mouth of a patient, wherein the resuscitator air supply pump and patient resuscitation mask have complementary friction fit connections, wherein the mask body is constructed of a transparent material whereby the user can visualize the newborn small animal patient's nose and mouth during resuscitation.

13. A method of aspirating and resuscitating a newborn small companion animal patient comprising the steps of:
   a. aspirating the patient by
      i. providing a hand-held, hand powered aspirator adapted to be held and operated by one hand, the aspirator including a suction pump connected to a patient aspiration mask, the aspirator further including
         a suction pump selectively connectible and disconnectible to a patient aspiration mask, the aspirator suction pump having a piston pump body with a suction port for connection to the patient aspiration mask and a pump actuator including an exhaust port, and the patient aspiration mask having a mask body with a pump connection end for mating with the aspirator suction pump and a flexible diaphragm disposed at an opposite end with an diaphragm aperture for placement on the nose or mouth of a newborn small animal patient,
      ii. placing the patient aspiration mask on the muzzle of the newborn small animal patient and
      iii. holding the aspirator in one hand and actuating the suction pump by hand power; and
   b. resuscitating the newborn small animal patient by
      i. providing a hand-held, hand powered resuscitator adapted to be held and operated by one hand, the resuscitator including an air supply pump connected to a patient resuscitation mask, the resuscitator further including:
         an air supply pump selectively connectible and disconnectible to a patient resuscitation mask, the resuscitator air supply pump having a piston pump body with an air ingress port and a pump actuator including an air egress port for connection to the patient resuscitation mask, the patient resuscitation mask having a mask body with a friction fit pump connection end for mating with the resuscitator air supply pump and a flexible diaphragm disposed at an opposite end with an diaphragm aperture for placement on the nose or mouth of the newborn small animal patient,
      ii. placing the patient resuscitation mask on the muzzle of the newborn small animal patient; and
      iii. holding the resuscitator in one hand and actuating the air supply pump by hand power.

* * * * *